US012611176B2

(12) United States Patent
Ossmann et al.

(10) Patent No.: US 12,611,176 B2
(45) Date of Patent: Apr. 28, 2026

(54) INTRALUMINAL IMAGING DEVICES WITH A REDUCED NUMBER OF SIGNAL CHANNELS

(71) Applicant: PHILIPS IMAGE GUIDED THERAPY CORPORATION, San Diego (CA)

(72) Inventors: William Ossmann, Acton, MA (US); Bernard Joseph Savord, Andover, MA (US); Wojtek Sudol, Andover, MA (US); Stephen Davies, El Dorado Hills, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 26 days.

(21) Appl. No.: 18/587,005

(22) Filed: Feb. 26, 2024

(65) Prior Publication Data

US 2024/0188931 A1     Jun. 13, 2024

Related U.S. Application Data

(63) Continuation of application No. 16/338,855, filed as application No. PCT/EP2017/074278 on Sep. 26, 2017, now Pat. No. 11,911,217.

(Continued)

(51) Int. Cl.
| | |
|---|---|
| *A61B 8/00* | (2006.01) |
| *A61B 8/08* | (2006.01) |
| *A61B 8/12* | (2006.01) |

(52) U.S. Cl.
CPC .......... *A61B 8/4461* (2013.01); *A61B 8/0883* (2013.01); *A61B 8/12* (2013.01);
(Continued)

(58) Field of Classification Search
CPC ................................ A61B 8/12; A61B 8/0883
See application file for complete search history.

(56) References Cited

U.S. PATENT DOCUMENTS

| | | |
|---|---|---|
| 6,468,216 B1 | 10/2002 | Powers et al. |
| 7,901,358 B2 | 3/2011 | Mehi et al. |

(Continued)

FOREIGN PATENT DOCUMENTS

| | | |
|---|---|---|
| WO | 2014080312 A1 | 5/2014 |
| WO | 2015150385 A2 | 10/2015 |

OTHER PUBLICATIONS

G. Gurun et al, "Front-End Receiver Electronics for High-Frequency Monolithic CMUT-on-CMOS Imaging Arrays", IEEE Transactions on Ultrasonics, Ferroelectrics, and Frequency Control, vol. 58, No. 8, pp. 1658-1668, Aug. 2011 (Year: 2011).*

(Continued)

*Primary Examiner* — Nyrobi Celestine

(57) ABSTRACT

An imaging assembly for an intraluminal imaging device is provided. In one embodiment, the imaging assembly includes an imaging array positioned at a distal portion of the intraluminal imaging device. The imaging array may have a plurality of imaging elements arranged into subarrays. The imaging assembly also may include a micro-beam-former integrated circuit (IC) coupled to the imaging array at the distal portion of the intraluminal imaging device. The micro-beam-former IC includes a plurality of microchannels that may separately beam-form signals received from imaging elements of at least two subarrays. The imaging assembly further includes two or more signal lines that may couple to the micro beam-former IC. Each signal line may correspond to a specific subarray and may receive the beam-formed signals specific to corresponding subarray.

12 Claims, 6 Drawing Sheets

Related U.S. Application Data

(60) Provisional application No. 62/437,778, filed on Dec. 22, 2016, provisional application No. 62/403,311, filed on Oct. 3, 2016.

(52) U.S. Cl.
CPC ............ *A61B 8/445* (2013.01); *A61B 8/4488* (2013.01); *A61B 8/466* (2013.01); *A61B 8/56* (2013.01)

(56) References Cited

U.S. PATENT DOCUMENTS

| | | | |
|---|---|---|---|
| 9,237,879 B2 | 1/2016 | Prins et al. | |
| 10,123,768 B2 | 11/2018 | Degertekin et al. | |
| 2005/0131302 A1 | 6/2005 | Poland | |
| 2005/0203410 A1 | 9/2005 | Jenkins | |
| 2007/0073154 A1 | 3/2007 | Karasawa | |
| 2007/0083119 A1 | 4/2007 | Adachi et al. | |
| 2008/0025145 A1 | 1/2008 | Peszynski et al. | |
| 2008/0146940 A1 | 6/2008 | Jenkins et al. | |
| 2008/0287803 A1* | 11/2008 | Li | A61B 5/064 |
| | | | 382/128 |
| 2009/0112091 A1 | 4/2009 | Chiang et al. | |
| 2009/0264759 A1 | 10/2009 | Byrd | |
| 2010/0168583 A1 | 7/2010 | Dausch et al. | |
| 2011/0172537 A1 | 7/2011 | Hongou et al. | |
| 2011/0245677 A1 | 10/2011 | Sato | |
| 2012/0095348 A1 | 4/2012 | Warnking | |
| 2012/0179043 A1 | 7/2012 | Kim et al. | |
| 2013/0128702 A1* | 5/2013 | Degertekin | A61B 8/445 |
| | | | 367/140 |
| 2013/0245450 A1 | 9/2013 | Prins et al. | |
| 2013/0267853 A1 | 10/2013 | Dausch et al. | |
| 2014/0180120 A1 | 6/2014 | Hossack | |
| 2014/0187965 A1 | 7/2014 | Reiter | |
| 2015/0209007 A1* | 7/2015 | Garbini | A61B 8/12 |
| | | | 600/459 |
| 2015/0289854 A1* | 10/2015 | Cho | H05K 1/0204 |
| | | | 600/463 |
| 2016/0135790 A1 | 5/2016 | Von Ramm et al. | |
| 2016/0136686 A1 | 5/2016 | Brock-Fisher | |
| 2016/0249882 A1 | 9/2016 | Degertekin et al. | |
| 2016/0325024 A1* | 11/2016 | Lin | A61L 29/145 |
| 2018/0064415 A1 | 3/2018 | Zhai et al. | |
| 2018/0264519 A1* | 9/2018 | Sudol | H01R 9/0515 |
| 2019/0274658 A1* | 9/2019 | Stigall | A61B 8/4461 |

OTHER PUBLICATIONS

C. Tekes et al, "Volumetric Imaging Using Single Chip Integrated CMUT-on-CMOS IVUS Array", 34th Annual International Conference of the IEEE Embs, pp. 3195-3198, Sep. 2012 (Year: 2012).*

G. Gurun et al, "Single-Chip CMUT-on-CMOS Front-End System for Real-Time Volumetric IVUS and ICE Imaging", IEEE Transactions on Ultrasonics, Ferroelectrics, and Frequency Control, pp. 239-250, vol. 61, No. 2, Feb. 2014 (Year: 2014).*

A. Nikoozadeh, "Intracardiac Ultrasound Imaging Using Capacitive Micromachined Ultrasonic Transducer (CMUT) arrays", Stanford University, pp. i-175, https://stacks.stanford.edu/file/druid:pq734dz2850/AminThesis-augmented.pdf, Dec. 2010 (Year: 2010).*

K. Chen, "A Column-Row-Parallel ASIC Architecture for 3D Wearable / Portable Medical Ultrasonic Imaging", pp. 1-174, Massachusetts Institute of Technology, https://dspace.mit.edu/bitstream/handle/1721.1/87916/880139231-MIT.pdf?sequence=2&isAllowed=y, Feb. 2014 (Year: 2014).*

M. Rashid et al., "Front-End Electronics for Cable Reduction in Intracardiac Echocardiography (ICE) Catheters", 2016 IEEE International Ultrasonics Symposiu, (IUS), pp. 1-4, Sep. 2016, (Year: 2016).

* cited by examiner

600

602 Receive ultrasound signals at an array of imaging elements

604 Beamform ultrasound signals received by a first subarray of the imaging elements 606 Beamform ultrasound signals received by a second subarray of the imaging elements 608 Transmit a first beam-formed signal over a first signal line 610 Transmit a second beam-formed signal over a second signal line

INTRALUMINAL IMAGING DEVICES WITH A REDUCED NUMBER OF SIGNAL CHANNELS

RELATED APPLICATIONS

This application is a continuation of application Ser. No. 16/338,855, filed Apr. 2, 2019, now U.S. Pat. No. 11,911, 217, which is the U.S. National Phase application under 35 U.S.C. § 371 of International Application No. PCT/EP2017/ 074278, filed on Sep. 26, 2017, which claims the benefit of and priority to Provisional Application Ser. No. 62/403,311, filed Oct. 3, 2016, and 62/437,778, filed Dec. 22, 2016, which are incorporated by reference in their entireties.

TECHNICAL FIELD

The present disclosure relates generally to intraluminal imaging devices and, in particular, to array-based intraluminal imaging devices with a reduced number of signal lines.

BACKGROUND

Diagnostic and therapeutic ultrasound catheters have been designed for use inside many areas of the human body. In the cardiovascular system, a common diagnostic ultrasound methods is intraluminal ultrasound imaging with intra-cardiac echocardiography (ICE) being a specific example of intraluminal imaging. Typically a single rotating transducer or an array of transducer elements is used to transmit ultrasound at the tips of the catheters. The same transducers (or separate transducers) are used to receive echoes from the tissue. A signal generated from the echoes is transferred to a console which allows for the processing, storing, display, or manipulation of the ultrasound-related data.

Intraluminal imaging catheters such as ICE catheters are usually used to image heart and surrounding structures, for example, to guide and facilitate medical procedures, such as transseptal lumen punctures, left atrial appendage closures, atrial fibrillation ablation, and valve repairs. Commercially-available ICE catheters have distal ends which can be articulated by a steering mechanism located in a handle at the proximal end of the catheter. For example, an intraluminal imaging catheter such as an ICE catheter may be inserted through the femoral or jugular vein when accessing the anatomy, and steered in the heart to acquire images necessary to the safety of the medical procedures.

An ICE catheter typically includes imaging transducers for ultrasound imaging that generates and receives acoustic energy. The imaging core may include a lined array of transducer elements or transducer elements arranged in any suitable configuration. The imaging core is encased in an imaging assembly located at a furthest distal tip of the catheter. The imaging assembly is covered with acoustic adhesive materials. An electrical cable is soldered to the imaging core and extends through the core of the body of the catheter. The electrical cable may carry control core signals and echo signals to facilitate imaging of the heart anatomy. The assembly may provide rotational, 2-way, or 4-way steering mechanisms such that anterior, posterior, left, and/ or right views of the heart anatomy may be imaged.

ICE imaging transducers are well known (e.g. Siemens Acunav, St. Jude ViewFlex). These transducers are introduced to the interior of the heart via a blood vessel by means of a catheter. ICE transducers may use a phased array sensor comprising many small individual transducers, each with a separate wire connecting the catheter to the imaging console. Up to 128 wires may be needed, leading to high cost, difficult manufacturing, and compromised image quality.

In phased array ICE transducers large number of wires can be brought up the catheter from the ICE transducer to the imaging system. A typical ICE transducer might have 128 transducers and 128 wires individually coupled to the transducers. These wires can all fit inside a catheter with a typical outer diameter of about 3 mm. The requirement to have so many wires in such a small diameter effectively precludes the use of coaxial cables for the wires as used in larger ultrasound imaging transducers. Without coaxial cables there is more crosstalk between signal channels and more interference from external noise sources, both of which will degrade the ultrasound image. Additionally, the wires can be individually connected to the elements of the transducer in a compact configuration to fit within the catheter tip. This difficult interconnect operation raises the cost of the transducer and is prone to errors and damage. Once assembled, the fine wires are prone to breaking due to flexure in normal use, decreasing the overall reliability of the transducer.

Another problem with the current art ICE transducers is that most of them create only 2D images while clinicians would like to have the possibility of 3D images. The only 3D ICE transducer currently available has only a small field of view and compromised image quality. Micro-beam-forming is a technology that is used in larger ultrasound imaging transducers (e.g. Philips xMatrix, Clearvue, and Lumify transducer lines) both to create 3D images and to reduce the number of wires required.

SUMMARY

The demand for higher quality intraluminal images for ICE procedures requires the development of miniaturized imaging elements and catheter components. One of the challenges is to create an imaging assembly configured to fit into a catheter that is also capable of high-throughput processes, such as micro-beam-forming.

The present disclosure solves that challenge by providing an ultrasound assembly that includes an integrated circuit (IC) with a small number of channels. Particularly, the integrated circuit is configured to perform beam-forming processes, but is designed so that the number of wires required is less than for typical micro-beam-formed transducers. The reduction in wire count enables 3D imaging, use of coaxial cable, higher manufacturing yield, reduced materials cost, and simpler, more easily manufactured electrical interconnect.

In some embodiments, the micro-beam-forming connections to the ultrasonic elements are simplified, e.g. by flip-chip mounting of the elements directly to the IC. This is advantageous for 2D imaging transducers and nearly essential for 3D imaging. Also, the number of wires required is reduced. Signal processing gains, especially for 3D imaging come from having the micro-beam-former's transmitters and receivers directly attached to the transducer elements rather than at the end of a long cable. However, the IC requires digital control lines, electrical power, and a number of discrete capacitors for noise decoupling and energy storage for those power supplies. This creates a new interconnect problem to connect all of the signal wires, capacitors, and power supply lines to the IC. In larger micro-beam-formed transducers a combination of flexible and rigid printed circuits is typically used to connect to I/O pads along one or more edges of the IC. In an ICE transducer, the entire assembly may fit inside of the catheter tip which typically has a diameter of only 3 mm compared to the 2-5 cm diameter of the larger transducers. Additionally, due to the small diameter of the catheter, it is desirable to have the short dimension of the acoustic aperture fill the diameter as much as possible, so it is not desirable to use any of that dimensions (the long sides of the IC) for interconnect. This limits the interconnect to be at the ends of the IC which are short, typically no more than 2.5 mm. Additionally, it may be impossible to use both ends of the IC due to difficulties of routing the wires to both ends simultaneously. The limitation of using only one edge of less than 2.5 mm severely limits the number of connections that can be made. Due to size restrictions inside the catheter, probably only one row of I/O pads could be connected along that edge, so a maximum of about 30 connections could be made with modern bonding equipment. Practical considerations related to processing the catheter can force even a smaller number.

Embodiments of the present disclosure provide an imaging assembly for an intraluminal imaging device. The imaging assembly includes an imaging array positioned at a distal portion of the intraluminal imaging device. The imaging array has a plurality of imaging elements arranged into subarrays. The imaging assembly also includes a micro-beam-former integrated circuit (IC) coupled to the imaging array at the distal portion of the intraluminal imaging device. The micro-beam-former IC includes a plurality of micro-channels that may separately beam-form signals received from imaging elements of at least two subarrays. The imaging assembly further includes two or more signal lines that are coupled to the micro beam-former IC. Each signal line corresponds to a subarray and may receive the beam-formed signals specific to corresponding subarray.

In one embodiment, the array of imaging elements is an array of ultrasound imaging transducers that are directly flip-chip mounted to the micro-beam-former IC. In some examples, the transmitters and receivers of the imaging transducers are implemented on the micro-beam-former IC 304 and thus are directly attached to the transducers.

In one embodiment, a method of intraluminal imaging includes receiving ultrasound signals at an array of imaging elements positioned within a distal portion of an intraluminal imaging device. The method includes beam-forming the ultrasound signals received by a first plurality of imaging elements of a first subarray of the array of imaging elements to define a first beam-formed signal. The method also includes beam-forming the ultrasound signals received by a second plurality of imaging elements of a second subarray of the array of imaging elements to define a second beam-formed signal. The beam-forming, can be performed with a micro-beam-former integrated circuit (IC) that is coupled to the array of imaging elements. The method includes transmitting the first beam-formed signal over a first signal line of a cable of the intraluminal imaging device and also transmitting the second beam-formed signal over a second signal line of the cable of the intraluminal imaging device.

In some embodiments, the method further comprises generating 2D and 3D images from the transmitted signals by the intraluminal imaging device. In some embodiments, the micro-beam-former IC includes multiple microchannel delay lines, and the method further includes beam forming the first subarray and the second subarray of the array of imaging elements using the microchannel delay lines.

Embodiments of the present disclosure provide a transducer array for an imaging device. The transducer array includes a plurality of imaging elements and a beam-former. The beam-former may include a plurality of microchannels each having a delay. The microchannel delays may align signals from the plurality of imaging elements. The transducer array may also include a signal line that may receive and transmit the aligned signals to the imaging system.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
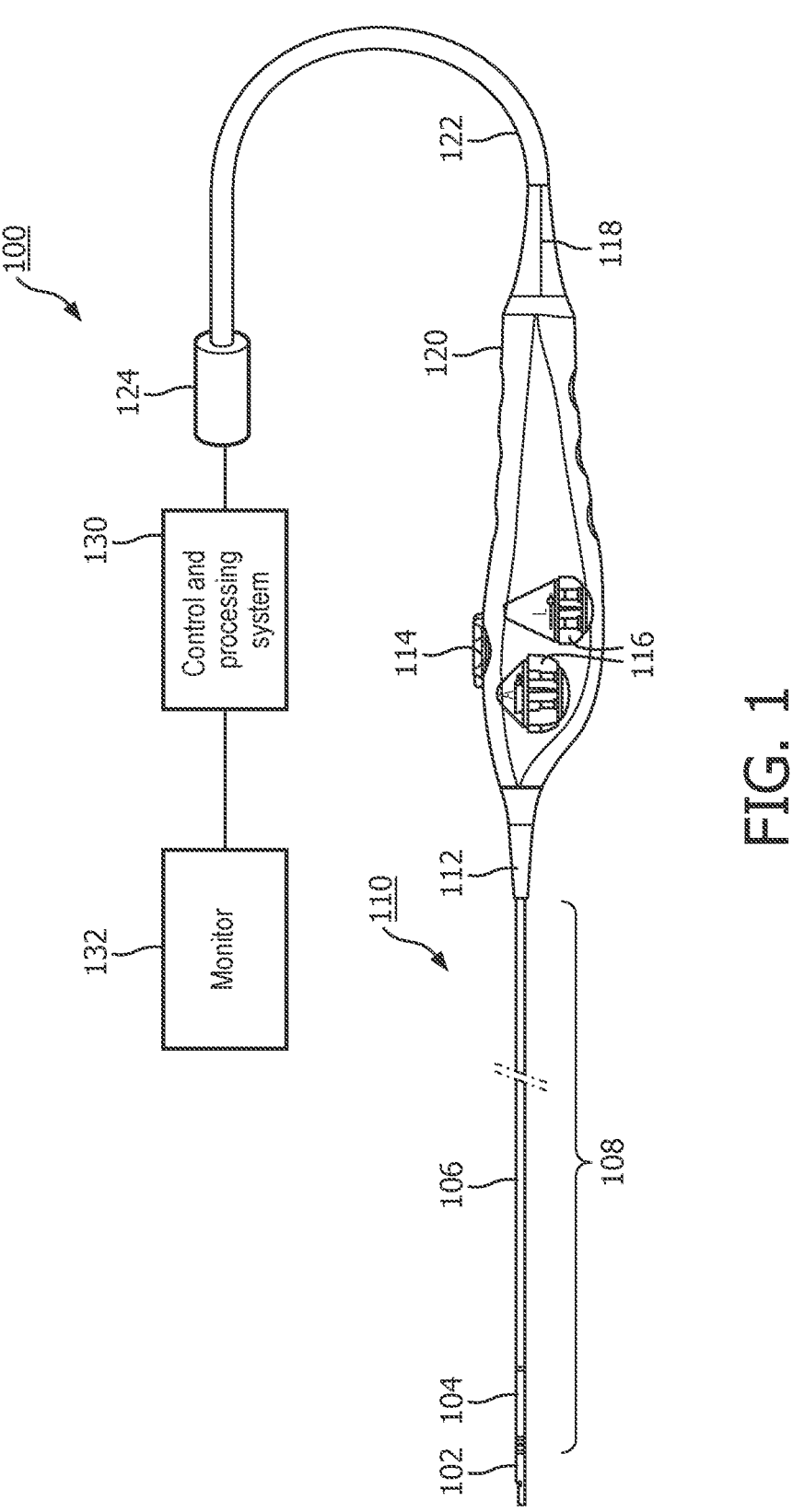
FIG. 1 is a schematic diagram of an intraluminal imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ICE system is described in terms of intraluminal imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100 according to embodiments of the present disclosure. The system 100 may include an intraluminal imaging device 110, a connector 124, a control and processing system 130, for example, a console and a computer, and a monitor 132. The intraluminal imaging device 110 includes an imaging assembly 102 at the tip of a flexible elongate member 108, and a handle 120. The flexible elongate member 108 includes a distal portion 104 and a proximal portion 106. The distal end of the distal portion 104 is attached to the imaging assembly 102. The proximal end of the proximal portion 106 is attached to the handle 120, for example, by a resilient strain reliever 112. The handle 120 may be used for manipulation of the intraluminal imaging device 110 and manual control of the intraluminal imaging device 110. The imaging assembly 102 can include an imaging core with ultrasound transducer elements and associated circuitry. The handle 120 can include actuators 116, a clutch 114, and other steering control components for steering the intraluminal imaging device 110. The steering may include deflecting the imaging assembly 102 and the distal portion 104, as described in greater details herein.

The handle 120 is connected to the connector 124 via another strain reliever 118 and a connection cable 122. The connector 124 may be configured to provide suitable configurations for interconnecting the control and processing system 130 and the monitor 132 to the imaging assembly 102. The control and processing system 130 may be used for processing, storing, analyzing, and manipulating data, and the monitor 132 may be used for displaying obtained signals generated by the imaging assembly 102. The control and processing system 130 can include one or more processors, memory, one or more input devices, such as keyboards and any suitable command control interface device. The control and processing system 130 can be operable to facilitate the features of the intraluminal imaging system 100 described herein. For example, a processor can execute computer readable instructions stored on the non-transitory tangible computer readable medium. The monitor 132 can be any suitable display device, such as liquid-crystal display (LCD) panel or the like.

In operation, a physician or a clinician may advance the flexible elongate member 108 into a vessel within a heart anatomy. By controlling the actuators 116 and the clutch 114 on the handle 120, the physician or clinician can steer the flexible elongate member 108 to a position near the area of interest to be imaged. For example, one actuator 116 may deflect the imaging assembly 102 and the distal portion 104 in a left-right plane and the other actuator 116 may deflect the imaging assembly 102 and the distal portion 104 in an anterior-posterior plane, as discussed in greater details herein. The clutch 114 provides a locking mechanism to lock the positions of the actuators 116 and in effect lock the deflection of the flexible elongate member while imaging the area of interest.

The imaging process may include activating the ultrasound transducer elements on the imaging assembly 102 to produce ultrasonic energy. A portion of the ultrasonic energy is reflected by the area of interest and the surrounding anatomy, and the ultrasound echo signals are received by the ultrasound transducer elements. The connector 124 transfers the received echo signals to the control and processing system 130 where the ultrasound image is reconstructed and displayed on the monitor 132. In some embodiments, the control processing system 130 can control the activation of the ultrasound transducer elements and the reception of the echo signals. In some embodiments, the control and processing system 130 and the monitor 132 may be part of a same system.

The system 100 may be utilized in a variety of applications such as transseptal punctures, left atrial appendage closures, atrial fibrillation ablation, and valve repairs and can be used to image vessels and structures within a living body. Although the system 100 is described in the context of intraluminal imaging procedures, the system 100 is suitable for use with any catheterization procedure, e.g., ICE. In addition, the imaging assembly 102 may include any suitable physiological sensor or component for diagnostic, treatment, and/or therapy. For example, the imaging assembly can include an imaging component, an ablation component, a cutting component, a morcellation component, a pressure-sensing component, a flow-sensing component, a temperature-sensing component, and/or combinations thereof.

In some embodiment, the intraluminal imaging device 110 includes a flexible elongate member 108 that can be positioned within a vessel. The flexible elongate member 108 may have a distal portion 104 and a proximal portion 106. The intraluminal imaging device 110 includes an imaging assembly 102 that is mounted within the distal portion 104 of the flexible elongate member 108.

In some embodiments, the intraluminal imaging system 100 is used for generating 2D and 3D images. In some examples, the intraluminal imaging system 100 is used for generating X-plane images at two different viewing directions perpendicular to each other.

Figure 2:
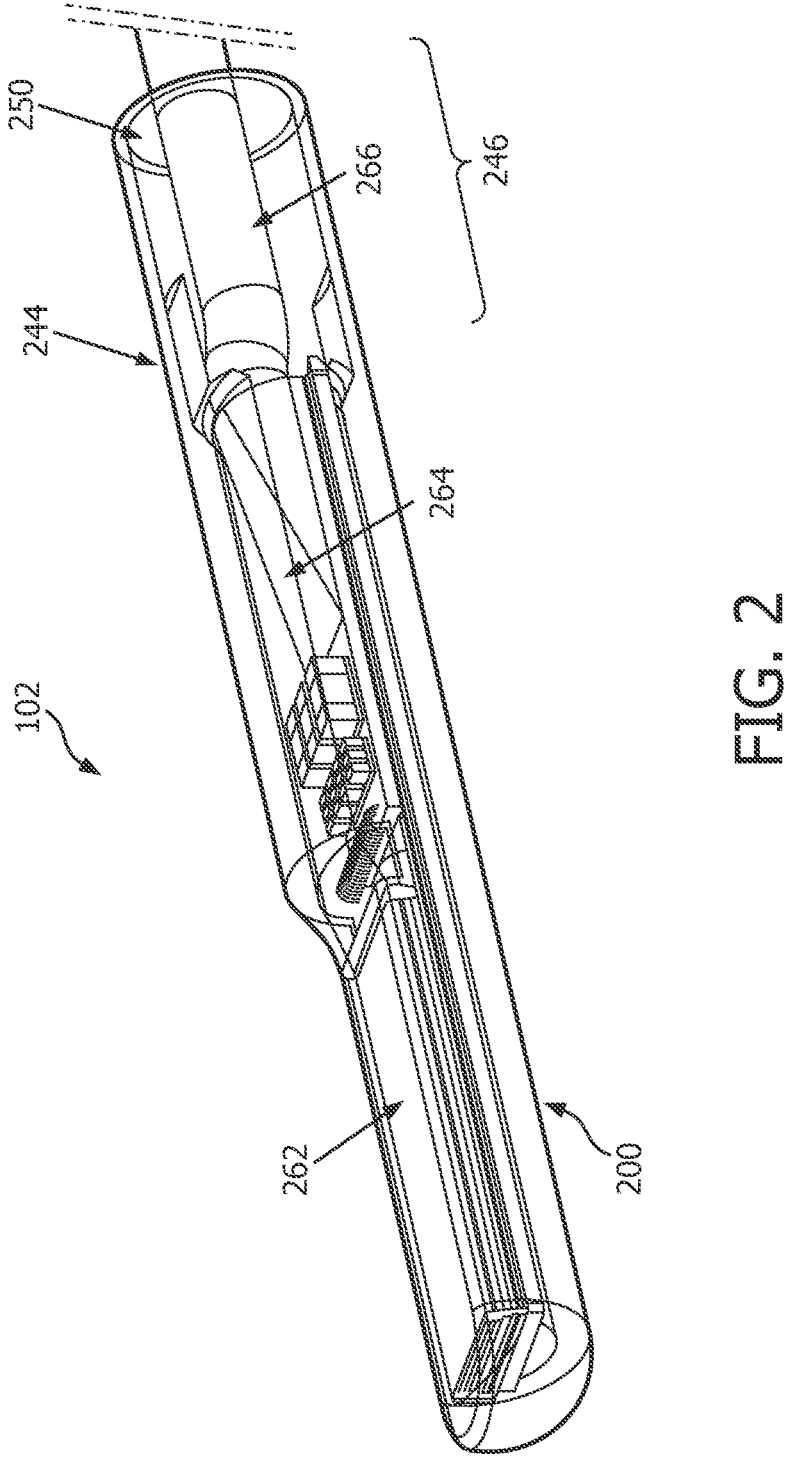
FIG. 2 is a perspective view of an imaging assembly according to embodiments of the present disclosure.

FIG. 2 is a perspective view of the imaging assembly 102 described above with respect to FIG. 1. The imaging assembly 102 may include the imaging core 262 that is positioned within a tip member 200. The imaging core 262 is coupled to an electrical cable 266 via an electrical interconnection 264. The electrical cable 266 extends through the alignment portion 244 and the interface portion 246 of the inner cavity 250. The electrical cable 266 can further extend through the flexible elongate member 108 as shown in FIG. 1.

The configuration and structure of the tip member 200 described above provide several benefits. The benefits include providing safe and easy delivery of the catheter, providing improved tensile strength for steering and navigation, providing consistent alignment, and providing improved image quality. For example, the outer geometry of the tip member 200 is configured to provide smooth surfaces and smooth edges with small radii. The smooth edges reduce friction when the tip member 200 traverses a vessel during insertion. The smooth surfaces prevent tears and/or damages to tissue structures during the insertion. In addition, the smooth edges and smooth surfaces can facilitate crossing of a septum or other anatomical feature during a catheterization procedure. In some embodiments, the material type and the wall thickness of the tip member 200 are selected to minimize acoustic distortion, attenuation, and/or reflection. The internal geometry of the tip member 200 is configured to facilitate alignment during manufacturing. The tip member 200 can also include other features, for example, a guidewire lumen, one or more holes, or other geometry to accommodate additional devices or features such as pressure sensors, drug delivery mechanisms, and/or any suitable interventional features.

Figure 3:
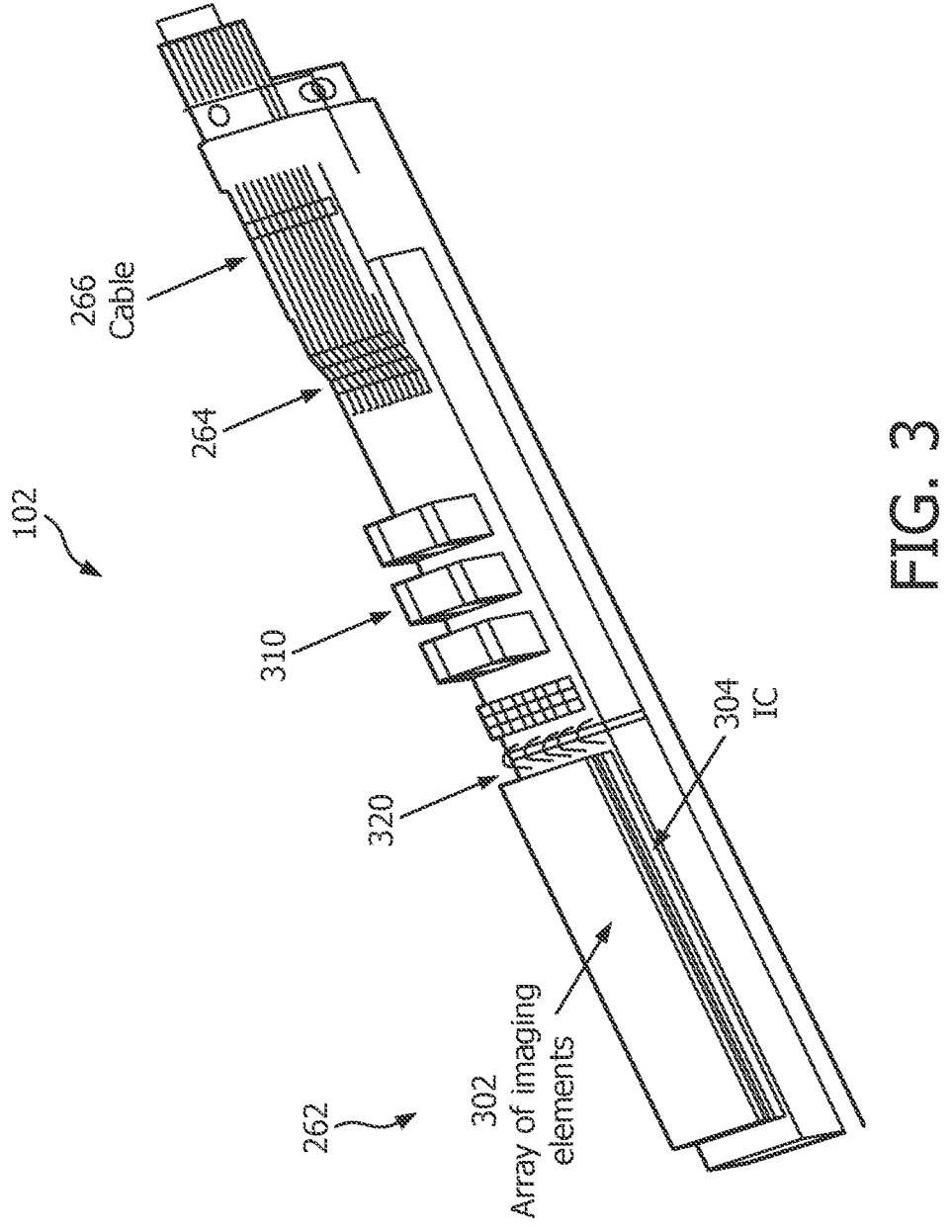
FIG. 3 is a top view of a tip member according to embodiments of the present disclosure.

FIG. 3 is a top view of the imaging assembly 102 according to embodiments of the present disclosure. The imaging assembly 102 may include the imaging core 262 having an array of imaging elements 302 and micro-beam-former IC 304 that can be coupled to the array of imaging elements 302. The imaging assembly 102 also shows the electrical cable 266 coupled to the electrical interconnection 264. In some examples, the electrical cable 266 is further coupled through an interposer 310 to the micro-beam-former IC 304. In some examples the interposer 310 is connected to the micro-beam-former IC 304 through wire bonding 320.

In some embodiments, the array of imaging elements 302 is an array of ultrasound imaging transducers that are directly flip-chip mounted to the micro-beam-former IC 304. The transmitters and receivers of the ultrasound imaging transducers are on the micro-beam-former IC 304 and are directly attached to the transducers. In some examples, a mass termination of the acoustic elements are done at the micro-beam-former IC 304.

In some examples, the imaging assembly 102 includes an array of imaging elements 302 in the form of an array of more than 800 imaging elements and the electrical cable 266 includes a total of 12 signal lines or less. In some examples, the electrical cable 266 includes a total of 30 lines or less that includes the signal lines, power lines, and control lines. In some examples, an array of imaging elements, for example a 1D or 2D array, may include between 32 to 1000 imaging elements. For example, the array can include 32, 64, 128, 256, 512, 640, 768, or any other suitable number of imaging elements. For example, a 1D array may have 32 imaging elements. A 2D array may have 32, 64, or more imaging elements. In some examples, the number of signal lines are between 10 and 20, for example, 12 signal lines, 16 signal lines, or any other suitable number of signal lines. A 1D array can be configured to generate 2D images. A 2D array can be configured to generate 2D and/or 3D images.

In some embodiments, the imaging assembly 102 include an ultrasound transducer array with fewer than 30 wires connecting to the control and imaging system 130. In certain embodiments, the 30 wires or less include 6-12 signal lines, preferably include 8 signal lines. In some examples, the transducer array is capable of 2D and 3D imaging. Additional aspects of the intraluminal imaging system includes a micro-beam-forming IC 304 with enough signal processing power to reduce the number of required ultrasound signal lines to a fraction of the total wires that include power and control lines.

In some examples, the electrical cable 266 of the imaging assembly 102 is directly coupled to the micro-beam-former IC 304 of the imaging assembly 102.

In some embodiments, the micro-beam-forming IC 304 lies directly underneath the array of acoustic elements 302 and is electrically connected to them. The array acoustic elements 302 may be piezoelectric or micromachined ultrasonic transducer (MUT) elements. In some examples, piezoelectric elements are attached to the IC 304 by flip-chip mounting of an assembly of acoustic layers that include sawing into individual elements. MUT elements may be flip-chip mounted as a unit or grown directly on top of the micro-beam-forming IC 304. In some examples, the cable bundle may be terminated directly to the micro-beam-forming IC 304, or may be terminated to an interposer 310 of suitable material such as a rigid or flexible printed circuit assembly. The interposer 310 may then be connected to the micro-beam-forming IC 304 via any suitable means such as wire bondings 320.

Figure 4:
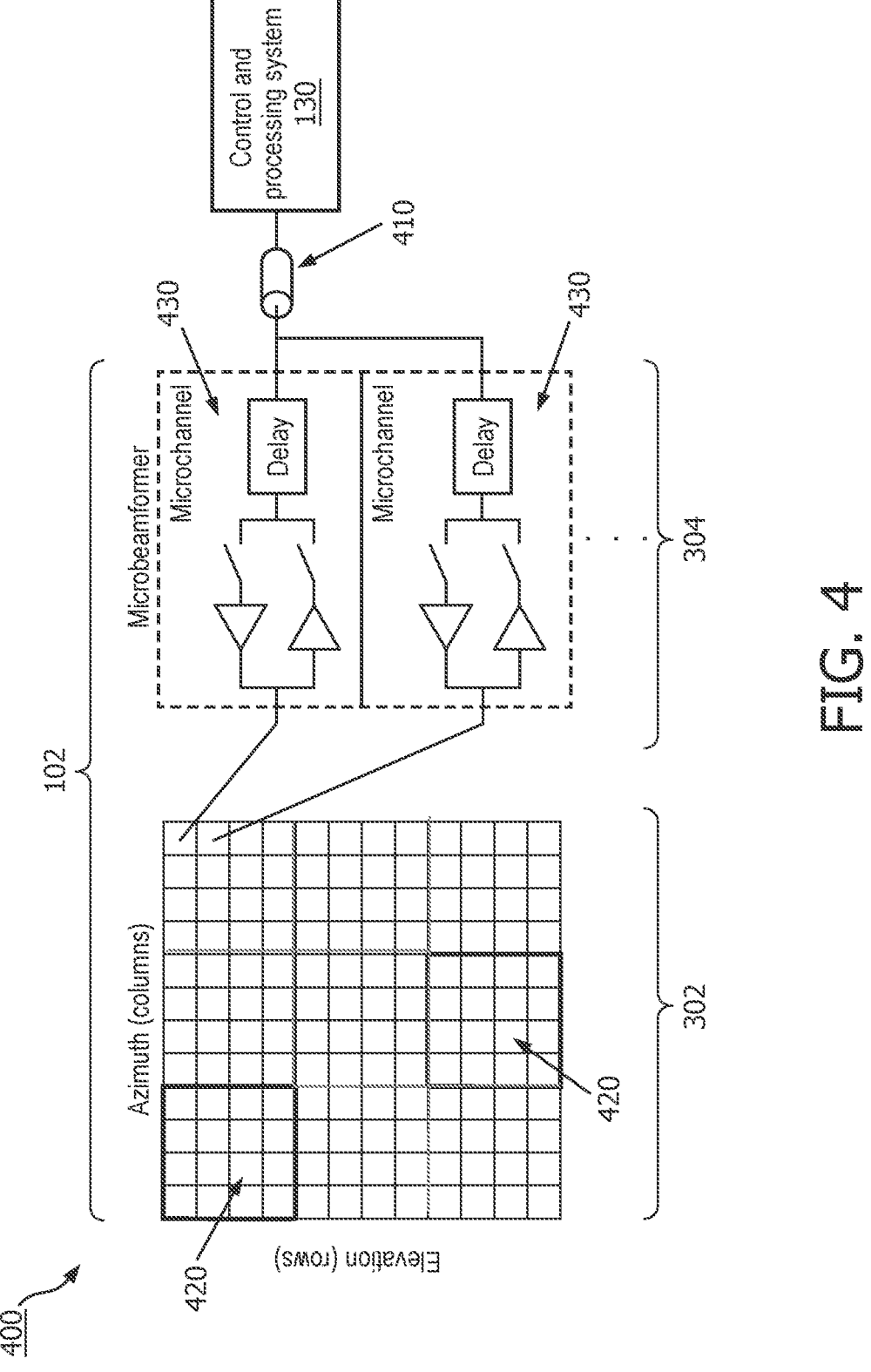
FIG. 4 is a schematic diagram illustrating the beam-forming of an intraluminal imaging device according to embodiments of the present disclosure.

FIG. 4 is a schematic diagram 400 illustrating the beam-forming of an intraluminal imaging device according to embodiments of the present disclosure. The diagram 400 includes the imaging assembly 102 that includes the array of imaging elements 302 and micro-beam-former IC 304. The micro-beam-former IC 304 can be coupled to the array of imaging elements 302 at the distal portion of an intraluminal imaging device (e.g., intraluminal imaging device 110). As shown, the array of imaging elements 302 is divided into one or more subarrays of imaging elements 420. For example, the array of imaging elements 302 are divided into 9 subarrays of imaging elements 420 that each has 16 imaging elements arranged as 4 by 4. The imaging assembly 102 also has the micro-beam-former IC 304 that includes a plurality of microchannels 430 that each can separately beam-form the signals received from imaging elements of a corresponding subarray 420. As shown in FIG. 4, for example, the microchannels 430 each comprise a delay for alignment of the signals received from the imaging elements of a subarray 420. As shown the microchannels delay lines 430 of each subarray of imaging elements 420 are separately coupled to one coaxial cable 410 such that the received signals of each subarray of imaging elements 420 are transferred through a separate channel, e.g., coaxial cable 410, to the control and processing system 130.

In some embodiments, the imaging assembly 102 includes an array of imaging elements 302. The array of imaging elements 302 can include two or more subarrays of imaging elements 420 of imaging elements. The imaging assembly 102 includes a micro-beam-former integrated circuit (IC) 304 coupled to the array of imaging elements.

In some examples, the micro-beam-former integrated circuit (IC) 304 can control the array of imaging elements 302 and can perform beam forming for a plurality of imaging elements of each subarrays of imaging elements 420 of the array of imaging elements 302.

In some embodiments, the imaging assembly 102 includes a cable 266 that includes two or more signal lines that are coupled to the micro-beam-former IC 304. Each of signal lines is associated with one of the subarrays of imaging elements 420 of the array of imaging elements 302 to transfer beam formed imaging signals of the associated subarray. For example, each signal line corresponds to a particular subarray 420 and is configured to receive the beam-formed signals specific to the corresponding subarray.

In some embodiments, the electrical cable 266 further includes one or more power lines for feeding power to the micro-beam-former IC 304 and one or more control lines for communicating control signals to the micro-beam-former IC 304.

In some examples, imaging assembly 102 includes an array of imaging elements 302 in the form of an array of more than 800 imaging elements such that the array of imaging elements is divided into no more than 12 subarrays of imaging elements 420 and the cable 410 includes no more than 12 signal lines, each signal line associated with one subarray of imaging elements 420.

In some embodiments, the array of imaging elements 302 is a two dimensional array. In some examples, the array of imaging elements 302 is symmetric such that it has equal number of rows of imaging elements and columns of imaging elements. In some other examples, the array of imaging elements 302 is asymmetric such that it has different number of rows of imaging elements and columns of imaging elements.

In some embodiments, the micro-beam-former IC 304 includes multiple microchannel delay lines 430. The micro-channel delay lines 430 are used to perform the beam forming for the plurality of imaging elements of each of the two or more subarrays of imaging elements 420. In some examples, the multiple microchannel delay lines 430 include at least one of a charge coupled device, an analog random access memory, or a tapped analog delay line.

In some examples, the first beam-formed signals and the second beam-formed signals are transmitted via a connection cable to a control and processing system 130 of FIGS. 1 and 4.

Figure 5:
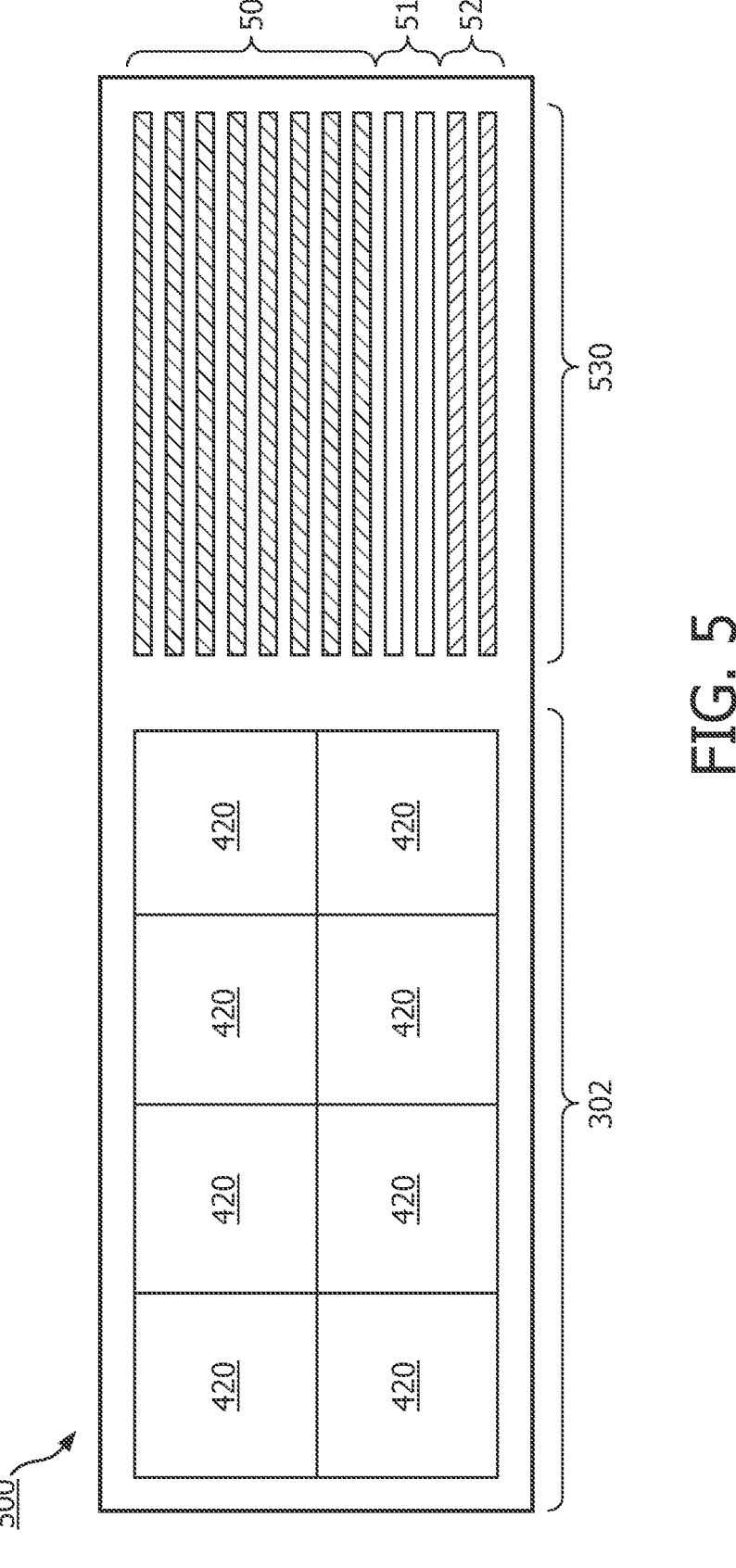
FIG. 5 is a schematic diagram illustrating aspects of an intraluminal imaging device according to embodiments of the present disclosure.

FIG. 5 is a schematic diagram illustrating aspects of an intraluminal imaging device according to embodiments of the present disclosure. The diagram 500 is consistent with imaging assemble 102 of FIGS. 1-4 that includes the array of imaging elements 302 and micro-beam-former IC 304. As shown, the array of imaging elements 302 is divided into subarrays of imaging elements 420. For example, the array of imaging elements 302 is divided into 8 subarrays of imaging elements 420. The imaging assembly 500 also shows the cable 530 which is consistent with the cables 410 and 266 in FIGS. 3 and 4 and includes 8 signal lines 505, two control lines 510 and 2 power lines 520. As shown there are 8 subarrays of imaging elements 420 and one signal line for each subarray of imaging elements 420 such that each signal line is associated with on subarray of imaging elements 420 such that the received signals of each subarray of imaging elements 420 are transferred through a separate signal lines 505 that can be consistent with the coaxial cable 410 of FIG. 4 to the control and processing system 130. As shown the power lines 520/control lines 510 can be coupled to one or more subarray of imaging elements 420 and can provide power/control one or more subarray of imaging elements 420.

In some embodiments, as shown in FIGS. 4 and 5, the overall aperture is divided into subarrays of imaging elements 420 each of which is independently beam-formed. A 2D array of imaging elements 302 is shown which can also be used for 3D imaging. The essential element in the micro-beam-former IC 304 is the delay in each microchannel 430. The delay is used to time-align the echoes received by each element in the subarray of imaging elements 420 so that the signals add constructively in the desired beam direction, but destructively in other directions. The delay may be of any convenient sort of controlled variable delay, such as charge coupled devices (CCD's), analog RAM, tapped analog delay lines, etc. The amount of delay $\tau$ required depends on the size of the subarray of imaging elements 420 and the maximum steering angle $\theta$:

$$\tau = d \sin\theta / v$$

where d is the maximum dimension of the subarray and $\theta$ is the maximum beam steering angle, and v is the speed of sound in the object that is being imaged. In some examples, the area of a subarray of imaging elements 420 is proportional to the square of its dimension, so the maximum subarray area A is proportional to the square of the available delay:

$$A \propto \tau^2$$

The larger the area of each individual subarrays of imaging elements 420, the fewer of them are needed to cover the entire acoustic aperture, the entire array of imaging elements 302. In some examples, each subarray of imaging elements 420 feeds one signal line through a single wire, thus, the number N of ultrasound signal wires required in the cable is inversely proportional to the square of the available delay:

$$N \propto 1/\tau^2$$

In some embodiments, the delay elements in use consist of a number of repeated elements, and the number of these elements determines the maximum available delay. Since the acoustic array is flip-chip mounted to the micro-beam-former IC 304, all of the processing, including the delay, for any given element can reside in the area occupied by that one element. In some examples, an ultrasound imaging catheter 2D array may have 1000 or more elements, so the number of ultrasound signal wires required would be in the range of 30 to 50, and 15 to 20 power and control lines might also be needed. This number of wires is typical in existing 1D ultrasound imaging catheters that use unshielded single wires rather than coaxial, and are individually attached to the acoustic elements. In some examples, the use of single wires rather than coax degrades the image due to noise susceptibility and crosstalk between the unshielded wires. In some examples, when using an IC within the catheter tip, the connections typically can be made to one narrow end of 2.5 mm, and so are limited to about 30 at most, including all of the ultrasonic signal lines, power lines, and control lines.

In some embodiments, newer IC processing equipment is now available which can approximately double the available amount of delay for the imaging signals, e.g., transducer signals. By the relations given above then the number of ultrasound signal wires could be reduced by about a factor of 4, to e.g., between 8 and 12. The total number of wires required is then in the range of 20 to 30, which is in the range of what that can be connected to the micro-beam-former IC 304, and allows the use of coaxial cables. In some examples, the reduced wire count has a number of advantages that include: having fewer interconnects in the flexible elongate member 108 tip, e.g., the catheter tip, decreases manufacturing cost and increases yield, and larger subarrays can track the depth of the received focal point in time.

In some examples, a possibly digital second beam-forming stage can be used that would further reduce the channel count. In some examples, cable count can further be reduced by implementing on-chip power regulation, sharing functions of wires, and using programmable autonomous IC controllers to reduce the number of power lines and control lines.

Figure 6:
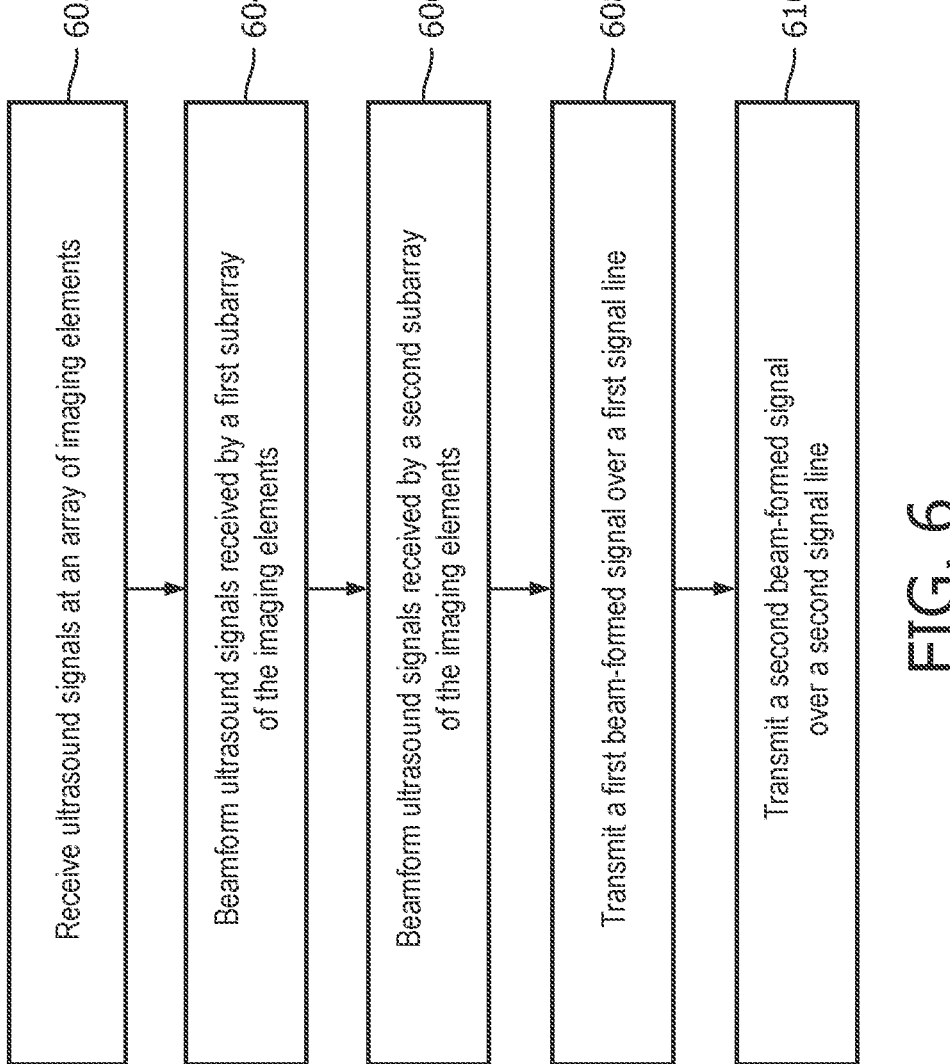
FIG. 6 is a flow diagram of a method of performing intraluminal imaging with an intraluminal device according to aspects of the disclosure.

FIG. 6 provides a flow diagram illustrating a method 600 of intraluminal imaging of a vessel. As illustrated, the method 600 includes a number of enumerated steps, but embodiments of the method 600 may include additional steps before, after, and in between the enumerated steps. In some embodiments, one or more of the enumerated steps may be omitted, performed in a different order, or performed concurrently. The method 600 can be performed with reference to FIGS. 1, 2, 3, and 4. At step 602, ultrasound signals are received at an array of imaging elements, e.g., the array of imaging elements 302. The array of imaging elements 302 can be positioned within the distal portion 104 of an intraluminal imaging device 110. In some examples, a micro-beam-former IC 304 is directly coupled to the array of imaging elements 302 and transmits and receives imaging signals, e.g., ultrasound signals.

At step 604 of the method 600 the ultrasound signals received by the first subarray of the array of imaging elements 302 are beam-formed. The beam-forming can be performed with reference to FIGS. 3 and 4. In some embodiments, the micro-beam-former IC 304 is coupled, e.g., from beneath, to the array of imaging elements 302. The micro-beam-former IC 304 can command the array of imaging elements 302 and can transmit and receive signals, e.g., ultrasound signals. In some examples, the array of imaging elements 302 are divided into a plurality of subarrays of imaging elements 420 including the first subarray. The micro-beam-former IC 304 can also include a plurality microchannels delay lines 430. The micro-beam-former IC 304 can supply the required delays for beam-forming from one of the microchannels delay lines 430 to the first subarray to provide beam-forming for the first subarray such that the beam-forming is provided by applying the required delays to the signals of each of the plurality of the imaging elements of the first subarray. In some examples, the beam-forming is performed during both transmitting and receiving. In some other examples, the beam-forming is performed during the receiving. In some examples, the ultrasound signals received by the plurality of imaging elements of the first subarray of the array of imaging elements are beam-formed by applying the required delays to construct a first beam-formed signal.

At step 606 of the method 600 the ultrasound signals received by the second subarray of the array of imaging elements 302 are beam-formed. The beam-forming can be performed with reference to FIGS. 3 and 4. The micro-beam-former IC 304 can supply the required delays for beam-forming from one of the microchannels delay lines 430 to the second subarray to provide beam-forming for the second subarray such that the beam-forming is provided by applying the required delays to the signals of each of the plurality of the imaging elements of the second subarray. In some examples, the ultrasound signals received by the plurality of imaging elements of the second subarray of the array of imaging elements are beam-formed by applying the required delays to construct a second beam-formed signal.

At step 608 of the method 600, the first beam-formed signal is transmitted over a first signal line of a cable of the intraluminal imaging device. This step can be performed with reference to FIG. 4. The beam-formed signal is constructed by applying the required beam-forming delays provided by a microchannels delay line 430 of the micro-beam-former IC 304 to the received signals of the first subarray of imaging elements 420 and then transmitting a collection of the received and delayed signals of the first subarray of imaging elements 420 through the cable, e.g., coaxial cable 410 to the control and processing system 130.

At step 610 of the method 600, the second beam-formed signal is transmitted over a second signal line of a cable of the intraluminal imaging device. Likewise, this step can be performed with reference to FIG. 4. The beam-formed signal is constructed by applying the required beam-forming delays provided by a microchannels delay line 430 of the micro-beam-former IC 304 to the received signals of the second subarray of imaging elements 420 and then transmitting a collection of the received and delayed signals of the second subarray 420 through a cable, e.g., a coaxial cable to the control and processing system 130. In some examples, the control and processing system 130 receives a plurality of the beam-formed signals from a plurality of the subarrays and constructs 2D and 3D images.

In some embodiments, the largest number of connections to a typical micro-beam-former IC 304 are the analog channel lines which carry the micro-beam-formed received signals back to the imaging system, and possibly transmit signals from the system 100 to the micro-beam-former IC. In some embodiments, large micro-beam-forming delays are produced on micro-beam-former IC 304 to reduce the number of analog channel lines compared to the existing micro-beam-former technology, thereby reducing the number of connections to the micro-beam-former IC 304 and the number of wires required to connect the imaging assembly 102 to the control and processing system 130. The reduced wire count has a number of advantages that include: reduced materials and assembly cost, reducing manufacturing cost and increasing yield, use of coaxial cables for transferring the signals and thus decreasing susceptibility to noise and crosstalk between channels that can degrade the image, ability to use larger wire size due to smaller number of wires and thus increasing reliability, providing 3D imaging capability, simplifying interconnect from the cable to the micro-beam-forming IC, and providing the potential for automating the interconnect processes.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus, comprising:
an intracardiac echocardiography (ICE) catheter comprising:
a flexible elongate member sized and shaped to be advanced through a blood vessel, wherein the flexible elongate member comprises a proximal portion, a distal portion, and a diameter;
an imaging assembly positioned at the distal portion and comprising:
an ultrasound transducer array comprising a plurality of transducer elements and configured to generate imaging signals;
an integrated circuit (IC) configured to receive the imaging signals, perform beamforming of the imaging signals, and output beamformed signals; and
a plurality of cables extending within the flexible elongate member and comprising a plurality of signal lines, at least one power line, and at least one control line;
a first type of electrical connection between the ultrasound transducer array and the IC configured to carry the imaging signals corresponding to a quantity of the plurality transducer elements before the beamforming is performed, wherein the first type of electrical connection comprises flip-chip mounting;
a second type of electrical connection between the imaging assembly and the plurality of cables configured to carry the beamformed signals corresponding to less than the quantity of the plurality of transducer elements after the beamforming is performed,
wherein a quantity of the plurality of cables is less than the quantity of the plurality of transducer elements.

2. The apparatus of claim 1, wherein the ultrasound transducer array is positioned directly on top of the IC.

3. The apparatus of claim 2,
wherein the IC comprises transmitters and receivers, and
wherein the first type of electrical connection is configured to establish direct communication between the plurality of transducer elements and the transmitters and the receivers.

4. The apparatus of claim 1, wherein the ultrasound transducer array comprises a two-dimensional, rectangular array extending in a long dimension and a short dimension.

5. The apparatus of claim 1, wherein the imaging assembly further comprises:
an interposer; and
a third type of electrical connection between the interposer and the IC configured to carry the beamformed signals corresponding to less than the quantity of the plurality of transducer elements after the beamforming is performed, wherein the third type of electrical connection comprises wire bonding.

6. The apparatus of claim 5, wherein the wire bonding is positioned at the distal portion of the interposer.

7. The apparatus of claim 5, wherein the second type of electrical connection comprises soldering between the interposer and the plurality of cables, wherein the soldering is positioned at the proximal portion of the interposer.

8. The apparatus of claim 1, wherein the quantity of the plurality of transducer elements comprises more than 800 transducer elements and less than 1000 transducer elements, and wherein the quantity of the plurality of cables comprises more than 16 cables and less than 30 cables.

9. The apparatus of claim 1, wherein the imaging assembly further comprises capacitors configured to provide at least one of noise decoupling or storage for energy supplied by the at least one power line.

10. The apparatus of claim 1, wherein the plurality of signal lines is configured to carry imaging signals generated by the ultrasound transducer array, wherein the at least one power line is configured to supply energy to at least one of the ultrasound transducer array or the IC, and wherein the at least one control line is configured to communicate control signals to the IC.

11. The apparatus of claim 1, further comprising a processor configured for communication with the ICE catheter and configured to generate ultrasound images of a heart.

12. The apparatus of claim 1, wherein an entirety of the imaging assembly is fit inside a diameter of the ICE catheter.

\* \* \* \* \*